US006555716B2

(12) United States Patent
Protzmann et al.

(10) Patent No.: US 6,555,716 B2
(45) Date of Patent: *Apr. 29, 2003

(54) PROCESS FOR THE HYDROFORMYLATION OF OLEFINS

(75) Inventors: Guido Protzmann, Marl (DE); Klaus-Diether Wiese, Haltern (DE); Wilfried Büschken, Haltern (DE); Dirk Röttger, Recklinghausen (DE)

(73) Assignee: Oxeno Olefinchemie GmbH, Marl (DE)

( * ) Notice: Subject to any disclaimer, the term of this patent is extended or adjusted under 35 U.S.C. 154(b) by 14 days.

This patent is subject to a terminal disclaimer.

(21) Appl. No.: 09/725,518

(22) Filed: Nov. 30, 2000

(65) Prior Publication Data

US 2001/0003785 A1 Jun. 14, 2001

(30) Foreign Application Priority Data

Nov. 30, 1999 (DE) .......................... 199 57 528

(51) Int. Cl.⁷ .................. C07C 45/00; C07C 29/14; C07C 29/16; C07C 27/20; C07C 51/16
(52) U.S. Cl. .................. 568/451; 568/454; 568/461; 568/463; 568/881; 568/882; 568/883; 568/885; 568/909; 568/909.5; 562/531
(58) Field of Search ................ 568/451, 454, 568/881, 882, 883, 885, 909, 909.5, 461, 463; 562/531

(56) References Cited

U.S. PATENT DOCUMENTS

| | | | | |
|---|---|---|---|---|
| 4,159,999 A | * | 7/1979 | Stautzenberger et al. ... | 260/604 HF |
| 4,214,109 A | * | 7/1980 | Carlock et al. .............. | 568/909 |
| 4,426,542 A | * | 1/1984 | Barker et al. ................ | 568/883 |
| 5,998,660 A | * | 12/1999 | Barner et al. ................ | 562/418 |
| 6,111,149 A | * | 8/2000 | Schwab et al. .............. | 568/904 |
| 6,184,424 B1 | | 2/2001 | Bueschken .................. | 568/882 |

FOREIGN PATENT DOCUMENTS

| | | |
|---|---|---|
| DE | 25 38 037 | 4/1977 |
| DE | 27 15 685 | 10/1977 |
| DE | 32 34 701 | 5/1984 |
| DE | 197 00 804 | 8/1998 |
| DE | 197 00 805 | 8/1998 |
| DE | 199 25 384 | 12/2000 |
| EP | 0 157 316 | 10/1985 |
| EP | 0 987 242 | 3/2000 |
| EP | 1 057 524 | 12/2000 |
| GB | 938831 | 10/1963 |
| GB | 938836 | 10/1963 |

OTHER PUBLICATIONS

B. Cornils, et al., Aqueous–Phase Organometallic Catalysis, pp. 308–310 and 316–317, "Two–Phase Hydroformylation of Higher Olefins with Rhodium/Triphenylphosphine Trisulfonate (TPPTS) as Catalyst System," 1998.
VDI Wärmeatlas, 7$^{th}$ Augmented Edition, pp. La 1—La 2, Lb 1 to Lb 7, Le 1 to Le 4, 1997.
S. Ergun, Chemical Engineering Progress, Carnegie Institute of Technology, vol. 48, No. 2, pp. 89–94, "Fluid Flow Through Packed Columns," Feb. 1952.
Y. Sato, et al., Journal of Chemical Engineering of Japan, vol. 6, No. 2, pp. 147–152, "Pressure Loss and Liquid Holdup in Packed Bed Reactor with Cocurrent Gas–Liquid Flow," 1973.
D.E. Sweeney, AIChE Journal, vol. 13, No. 4, pp. 663–669, "A Correlation for Pressure Drop in Two–Phase Cocurrent Flow in Packed Beds," Jul. 1967.
V.W. Weekman, Jr., et al., A.I.Ch.E. Journal, vol. 10, No. 6, pp. 951–957, "Fluid–Flow Characteristics of Concurrent Gas–Liquid Flow in Packed Beds," Nov. 1964.
R.P. Larkins, et al., A.I.Ch.E. Journal, vol. 7, No. 2, pp. 231–239, "Two–Phase Concurrent Flow in Packed Beds," Jun. 1961.
N. Midoux, et al., Journal of Chemical Engineering of Japan, vol. 9, No. 5, pp. 350–356, "Flow Pattern, Pressure Loss and Liquid Holdup Data in Gas–Liquid Downflow Packed Beds with Foaming and Nonfoaming Hydrocarbons," 1976.

* cited by examiner

Primary Examiner—Deborah D. Carr
Assistant Examiner—Sikarl A. Witherspoon
(74) Attorney, Agent, or Firm—Oblon, Spivak, McClelland, Maier & Neustadt, P.C.

(57) ABSTRACT

Aldehydes are prepared in a hydroformylation apparatus by the multiphase hydroformylation reaction of one or more olefins with hydrogen and carbon monoxide, where the continuous phase contains a solvent mixture and the hydroformylation catalyst is present in the continuous phase, at least one olefin is present in the dispersed phase, and the loading factor of the tube reactor is greater than or equal to 0.8.

15 Claims, 1 Drawing Sheet

PROCESS FOR THE HYDROFORMYLATION OF OLEFINS

BACKGROUND OF THE INVENTION

1. Field of the Invention

This invention is a process for preparing aldehydes having 3–26 carbon atoms by reacting olefins having 2–25 carbon atoms with hydrogen and carbon monoxide in the presence of a catalyst in a tube reactor.

2. Discussion of the Background

Aldehydes are used in the synthesis of many organic compounds, for example, alcohols and carboxylic acids. In addition, aldol condensation of aldehydes and subsequent hydrogenation of the condensate provides alcohols having twice the number of carbon atoms as the starting aldehydes. Alcohols prepared by the hydrogenation of aldehydes are used, for example, as solvents and as intermediates for the production of plasticizers and detergents.

It is known that aldehydes and alcohols can be prepared by reaction of olefins with carbon monoxide and hydrogen (i.e., hydroformylation, oxo process). The reaction is catalyzed by hydridometal carbonyls, preferably those containing metals of Group VIII of the Periodic Table. Apart from cobalt, which is widely used industrially as catalyst metal, rhodium has acquired increasing importance in recent times. In contrast to cobalt, rhodium allows the hydroformylation reaction to be carried out at low pressures, and the hydrogenation of the olefin starting materials to form saturated hydrocarbons takes place to a significantly lesser extent when using rhodium catalysts than when using cobalt catalysts.

In the industrial hydroformylation process, the rhodium catalyst is formed in situ from a catalyst precursor, synthesis gas and possibly other ligands. When using modified catalysts, the modifying ligands can be present in excess in the reaction mixture. Ligands which have been found to be particularly useful are tertiary phosphines or phosphites, which allow the reduction of the reaction pressure to values of significantly less than 300 bar.

However, separating off the reaction products and recovering the catalysts homogeneously dissolved in the reaction product are problems in this process. In general, the reaction product is distilled from the reaction mixture. However, because of the thermal sensitivity of the catalyst or the products formed, in practice, this route is possible only for the hydroformylation of lower olefins having 5 or less carbon atoms in the molecule.

Industrially, $C_4$- and $C_5$-aldehydes are prepared by hydroformylation, for example as described in DE 32 34 701 or DE 27 15 685.

In the process described in DE 27 15 685, the catalyst is dissolved in an organic phase comprising the product and high boilers formed from the product. Olefin and synthesis gas are added into this mixture. The product is carried from the reactor in the gas phase with the synthesis gas, or is taken off as a liquid. Since the activity of the catalyst slowly decreases over time, some of the catalyst has to be continually bled out of the reaction, together with high boilers, and replaced by an equivalent amount of fresh catalyst. Recovery of the rhodium from this bleed stream is absolutely necessary due to its high cost. A disadvantage of this process is the complexity of the isolation and purification of the product and recovery of the rhodium.

The process of DE 32 34 701 overcomes this disadvantage by dissolving the catalyst in water. The rhodium catalyst is solubilized in water by using trisulphonated triarylphosphine ligands. Olefin and synthesis gas are added to the aqueous catalyst phase, and the product produced by the reaction forms a second immiscible organic liquid phase. The liquid phases are separated from one another outside the reactor and the catalyst phase which has been separated off is returned to the reactor. However, this process provides lower space-time yields than processes in which the catalyst is dissolved in a liquid organic phase, because the catalyst is primarily soluble in the aqueous phase, whereas the olefins are primarily soluble in the organic phase, but are virtually insoluble in the aqueous phase. The already low solubility of the olefins in the aqueous phase decreases further with increasing molar mass of the olefins. As a result, higher aldehydes cannot be prepared economically by this process.

Addition of an organic solvent which is soluble in the aqueous catalyst phase increases the rate of the hydroformylation reaction. The use of alcohols such as methanol, ethanol or isopropanol as cosolvents increases the reaction rate, but has the disadvantage that the rhodium catalyst is then present in the product phase (B. Cornils, W. A. Herrmann, Aqueous-Phase Organometallic Catalysis, Wiley-VCH, p. 316–317) and is thus removed from the reactor. An increase in the reaction rate can also be achieved, for example, by addition of ethylene glycol. However, adding ethylene glycol reduces the selectivity of aldehyde formation since ethylene glycol can form acetal derivatives with the aldehyde (V. S. R. Nair, B. M. Bhanage, R. M. Deshpande, R. V. Chaudhari, Recent Advances in Basic and Applied Aspects of Industrial Catalysis, Studies in Surface Science and Catalysis, Vol. 113, 529–539, 1998 Elsevier Science B.V.).

EP 0 157 316 describes adding solubilizers such as carboxylic acid salts, alkyl polyethylene glycols or quaternary onium compounds to increase the reaction rate in the hydroformylation of 1-hexene. Depending on the solubilizer used, the productivity was increased by a factor of 4. Increasing the reaction rate by addition of polyglycols (e.g. PEG 400) and polyglycol ethers is also known. Thus, DE 197 00 805 C1 describes the hydroformylation of propene, 1-butene and 1-pentene, and DE 197 00 804 C1 describes the hydroformylation of higher olefins such as 1-hexene, 4-vinylcyclohexene, 1-octene, 1-decene or 1-dodecene. In both of these processes, the use of solubilizers does increase the reaction rate, but the separation of the aqueous catalyst phase and organic product phase is more difficult, which results in losses of catalyst due to the increased solubility of the catalyst in the organic phase, as well as losses of desired products which become soluble in the aqueous phase. If the amount of solubilizer is reduced to minimize these losses, the reaction rate is simultaneously reduced again.

DE 199 25 384 states that the space-time yield of aldehydes in the hydroformylation of olefins in a multiphase reaction, in which one of the phases is a continuous catalyst phase, can be improved if the reaction is carried out in a flow reactor at a loading factor B>0.8, rather than in a stirred reactor. This process for hydroformylating olefins by means of a multiphase reaction employs very high loading factors in the tube reactor, i.e., extremely high mixing of the phases. Phase transfer reagents, surface-active or amphiphilic reagents or surfactants can be added to the catalyst phase, and water is the preferred solvent for the catalyst.

It is therefore an object of the present invention to provide a process for hydroformylating olefins which provides high space-time yields and selectivities.

SUMMARY OF THE INVENTION

Surprisingly, it has been found that olefins may be the hydroformylated in a multiphase reaction, at high yields and with low formation of by-products, if the catalyst phase comprises a solvent mixture. The present invention accordingly provides a process for hydroformylating one or more olefins having from 2 to 25 carbon atoms by means of a multiphase reaction in a tube reactor, wherein a) the catalyst is present in the continuous phase, b) the continuous phase contains a solvent mixture, c) at least one olefin is present in the disperse phase, and d) the loading factor of the tube reactor is equal to or greater than 0.8.

In the present invention, the hydroformylation is carried out in a tube reactor, i.e. a flow tube. The catalyst phase and the dispersed phase containing at least one olefin are pumped into the tube reactor. After the reaction, the reaction mixture is separated into a product phase and a catalyst phase, and the catalyst phase is recirculated to the tube reactor. The product phase is removed, and the aldehydes can be isolated and purified by distillation. Aldehydes prepared by this process can be hydrogenated to prepare alcohols, used in aldol condensations, or oxidized to prepare carboxylic acids.

DETAILED DESCRIPTION OF THE INVENTION

The catalyst solution used in the process of the present invention contains a solvent mixture and a catalyst. Protic polar substances, for example water, ethylene glycol, 1,2-propylene glycol, 1,3-propylene glycol, butanediols or glycerol, may be used as one component of the solvent. A preferred solvent component is water.

Polar organic substances, particularly ones which contain at least two oxygen atoms, may be used as additional solvent components for forming the solvent mixture. For example, polar organic substances may be selected from diols, triols, polyols and their partial and full ethers. Such compounds may include, for example, ethylene glycol, ethylene glycol monoethers, ethylene glycol diethers, ethylene glycol ethoxylates, ethers or ethylene glycol ethoxylates, ethylene glycol propoxylates, monoethers and diethers of ethylene glycol propoxylates, propylene glycol propoxylates, their monoethers and diethers, polyols which can be produced by hydrogenation of carbohydrates (e.g. hydrogenated monosaccharides disaccharides, oligosaccharides), and their partial and full ethers. A solvent mixture of water and a water-miscible organic solvent containing at least two oxygen atoms can therefore be used as continuous phase in the process of the invention.

The mass ratio of the solvents in the solvent mixture can be varied within a wide range as long as the mixture forms a homogeneous solution (phase). The solubility of the catalyst in this homogeneous solution has to be sufficiently high so that the desired catalyst concentrations may be obtained. Furthermore, the solution viscosity must be low enough so that it does not impair the reaction and/or the subsequent phase separation.

Preferred solvent mixtures have a dielectric constant at 20° C. of from 50 to 78. Examples of such solvent mixtures are water/ethylene glycol mixtures as shown in the following table.

| % by weight of water | % by weight of ethylene glycol | Dielectric constant |
| --- | --- | --- |
| 80 | 20 | 74.65 |
| 70 | 30 | 72.19 |
| 60 | 40 | 69.11 |
| 50 | 50 | 65.42 |
| 0 | 100 | 37.89 |

Transition metals of Group VIII of the Periodic Table of the Elements, namely Fe, Co, Ni, Ru, Rh, Pd, Os, Ir and Pt, preferably in the form of complexes, may be used as hydroformylation catalysts. Under the reaction conditions, it is desirable that these metal compounds should be soluble in the catalyst phase, but not the product phase. Water-soluble metal compounds are required if aqueous catalyst solutions are used. Preferred catalysts are rhodium or water-soluble rhodium compounds. Suitable rhodium salts are, for example, rhodium(III) sulphate, rhodium(III) nitrate, rhodium(III) carboxylates such as rhodium acetate, rhodium propionate, rhodium butyrate or rhodium 2-ethylhexanoate.

The type of ligands used in the catalyst depends on both the metal with which they are complexed, and the solvent mixture in which they are used. These complexes should not lose their catalytic activity even when used over long periods of time. Accordingly, the ligands of the catalyst should not change over time, for example by reaction with the solvent.

Triarylphosphines may be used as ligands for the hydroformylation catalyst of the present invention. Suitable phosphines contain one or two phosphorus atoms and have three aryl groups per phosphorus atom; the aryl groups may be identical or different and are each at least one group selected from phenyl, naphthyl, biphenyl, phenylnaphthyl or binaphthyl groups. The aryl groups may be attached to the phosphorus atom either by a direct covalent bond or via a —$(CH_2)_x$ group, where x is an integer from 1 to 4, including 3, preferably 1 or 2, particularly preferably 1. For water-soluble catalyst systems, at least one ligand should contain from 1 to 3 —$(SO_3)M$ groups, where each M may be identical or different, and are selected from H, an alkali metal ion such as $Na^+$ or $K^+$, an ammonium ion, a quaternary ammonium ion, a alkaline earth metal ion such as $Ca^{2+}$, $Mg^{2+}$, or $Zn^{2+}$ (when the metal ion has an oxidation number of 2, there are two —$(SO_3)M$ groups per metal ion). The —$(SO_3)M$ groups are usually substituents on the aryl groups and impart the required water solubility to the triarylphosphine ligands. A preferred sulphonated triarylphosphine having one phosphorus atom is trisodium tri(m-sulphophenyl)phosphine. In addition, instead of being substituted by sulphonato units (i.e., —$SO_3M$), the phosphines can also be substituted by other polar groups such as carboxylato units.

The solvent mixture can be introduced directly, i.e., without the catalyst, into the hydroformylation reactor. Alternatively, it may also be possible to form the catalyst beforehand in the solvent mixture, then add the solvent mixture containing the preformed catalyst to the hydroformylation reactor. However, if the solvent mixture contains water, the catalyst solution can also be prepared in a comparatively simple manner by dissolving a water-soluble metal salt and/or the water-soluble ligands in water, forming the complex, then subsequently adding an additional solvent or solvents to form the solvent mixture.

The metal salt concentration used in the process of the present invention can vary over a wide range, with the reaction rate also depending on the metal salt concentration. In general, higher reaction rates are achieved at higher metal salt concentrations, but higher metal salt concentrations incur higher costs. An optimum can therefore be selected which depends on the reactivity of the starting material and the other reaction conditions. This optimum can be determined readily by means of preliminary experiments. If rhodium is used as the active catalyst, the rhodium content of the catalyst phase is usually from 20 ppm to 2000 ppm, including 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, and 1900 ppm, inclusive of all values and subranges therebetween. Preferably, the rhodium content of the catalyst phase is from 100 to 1000 ppm. The molar ratio of metal to ligands can be varied in order to achieve the optimum results for each individual reaction. This metal/ligand ratio is generally from 1/5 to 1/200, including 1/10, 1/20, 1/30, 1/40, 1/50, 1/60, 1/70, 1/80, 1/90, 1/100, 1/110, 1/120, 1/130, 1/140, 1/150, 1/160, 1/170, 1/180, and 1/190, inclusive of all values and subranges therebetween. In particular, the metal/ligand ratio may be from 1/10 to 1/60.

The pH of the catalyst solution can be optimized for the hydroformylation of each olefin so as to give the best selectivity of aldehyde formation. The pH is generally from 2 to 8, including 2.5, 3.0, 3.5, 4.0, 4.5, 5.0, 5.5, 6.0, and 7.5, inclusive of all values and subranges therebetween. Preferably, the pH is from 3.0 to 5.5. The pH can be adjusted while the process is running by, for example, addition of a sodium hydroxide solution or a sulphuric acid solution.

Olefinic compounds having 2–25 carbon atoms, including 3, 4, 5, 6, 7, 8, 9, 10, 11, 12, 13, 14, 15, 16, 17, 18, 19, 20, 21, 22, 23, and 24 carbon atoms may be used in the process of the invention. The olefinic compounds preferably have 3–12 carbon atoms. The olefinic compounds can contain one or more carbon—carbon double bonds which may each be terminal or internal. Olefinic compounds having a terminal carbon—carbon double bond are preferred. It is possible to use a single type of olefin, but olefin mixtures can also be used. The mixture can consist of isomeric olefins having the same number of carbon atoms or of olefins having different numbers of carbon atoms or of a mixture containing both isomeric olefins and olefins having a different number of carbon atoms. Furthermore, the olefins or olefin mixtures can contain materials which are inert under the reaction conditions, for example aliphatic hydrocarbons. The olefins, together with any inert materials present preferably form the dispersed phase.

Olefins obtained from a wide variety of sources may be used in the process of the present invention. For example, olefins from cracking processes, dehydrogenations or from a Fischer-Tropsch synthesis may be employed. Olefins or olefin mixtures formed by dimerization, oligomerization, codimerization, cooligomerization or the metathesis of olefins are likewise suitable starting materials.

The olefins used may be gasses, liquids or solids (e.g., at approximately room temperature and about one atmosphere pressure). Solid olefins are dissolved in inert liquid solvents which are insoluble or only slightly soluble in the catalyst phase. Solvents which have a higher boiling point than that of the expected products are particularly preferred, since this makes separation of the products by distillation and recirculation easier.

In the process of the present invention, α-olefinic compounds are preferred. Examples of suitable α-olefinic compounds are 1-alkenes, alkyl alkenoates, alkenyl alkanoates, alkenyl alkyl ethers and alkenols, e.g., propene, butene, pentene, butadiene, pentadiene, 1-hexene, 1-heptene, 1-octene, 1-nonene, 1-decene, 1-undecene, 1-dodecene, 1-hexadecene, 2-ethyl-1-hexene, 1,4-hexadiene, 1,7-octadiene, 3-cyclohexyl-1-butene, styrene, 4-vinylcyclohexene, allyl acetate, vinyl formate, vinyl acetate, vinyl propionate, allyl methyl ether, vinyl methyl ether, vinyl ethyl ether, allyl alcohol, 3-phenyl-1-propene, hex-1-en-4-ol, oct-1-ene-ol, 3-butenyl acetate, allyl propionate, allyl butyrate, n-propyl 7-octenoate, 7-octenoic acid, 5-hexenamide, 1-methoxy-2,7-octadiene and 3-methoxy-1,7-octadiene. Particularly suitable olefins are propene, 1-butene or industrially available olefin mixtures containing essentially 1-butene, 2-butene and 1-butene, and/or 1-pentene.

The products of the hydroformylation of olefins are aldehydes having one more carbon atoms than the olefin starting material, and possibly the corresponding alcohols which are formed by hydrogenation of the product aldehyde during the hydroformylation process. The aldehydes prepared by the process of the invention can, however, also be hydrogenated in a separate step to form the corresponding saturated alcohols. These saturated alcohols can be used as solvents or as raw materials for producing detergents or plasticizers.

The hydroformylation agent used in the process of the present invention is a mixture of hydrogen and carbon monoxide (synthesis gas) or a mixture of hydrogen, carbon monoxide and other materials which are inert under the reaction conditions. Synthesis gas containing 50% by volume of $H_2$ and 50% by volume of CO is preferred.

When using liquid olefins or solid olefins in solution, it is useful to have an excess of the hydroformylation agent so that as complete as possible a conversion is achieved. This reduces the costs of the subsequent isolation and purification steps (i.e., "work-up"). In contrast, when using gaseous olefins, it may be useful to employ a deficiency in the amount of hydroformylation reagent, since the excess gaseous olefin is easily separated and returned to the process from the liquid product phase. In each case, the molar ratio of olefin to hydrogen and of olefin to carbon monoxide can be greater than, smaller than, or equal to 1.

When using a gaseous olefin, the process of the invention is initially a two-phase reaction, but a liquid product phase forms during the reaction, thereby forming a three-phase system. When using a liquid olefin, at least three phases are present from the beginning of the reaction.

The tube reactor used in the process of the present invention can contain packing or internal fittings. Examples of such packing materials are: Raschig rings, saddles, Pall rings, tellerettes, wire mesh rings or woven wire mesh. Examples of internal fittings are filter plates, baffles, column trays, perforated plates or other mixing devices. In addition, internal fittings can also comprise a plurality of narrow, parallel tubes to form a multitube reactor. Particular preference is given to structured mixer packings or demister packings.

In the process of the present invention, it is also of critical importance to adhere to or exceed a minimum cross-sectional throughput or loading factor B of the tube reactor. When the reactor is operated in an upflow mode (flow direction from the bottom of the reactor to the top of the reactor), the flooding point should be exceeded. The reactor is thus operated above the point at which bubble columns are usually operated. When operated in a downflow mode (flow direction from the top of the reactor to the bottom of the reactor), the cross-sectional throughput must be set so that the reactor is completely flooded. Thus, the process is operated above the point at which it would still be possible to speak of a trickle bed.

To more precisely fix the minimum necessary loading of the reactor, the loading factor B of the tube reactor is calculated as a dimensionless pressure drop $$B=PD/PS$$

where PD (Pa/m) is a pressure drop per unit length over the reactor under the operating conditions and PS (Pa/m) is a mathematical parameter having the dimensions of a pressure per unit length, defined as the ratio of mass flow M (kg/s) of all components in the reactor to the volume flow V (m$^3$/s) of all components under operating conditions, multiplied by g=9.81 m/s$^2$, i.e., PS=(MV)g. To put it in concrete terms, PS would be the static pressure per meter of a multiphase mixture in an upright tube if all phases were to flow at the same velocity. PS is a purely mathematical parameter which is derived from the mass flows fed to the reactor and is independent of the flow direction in the reactor, the flow velocity of all phases or the flooding state of the reactor.

The pressure drop PD (Pa/m) is used as a mathematical parameter to fix the process conditions and can be calculated by established methods for single-phase or multiphase flows. Appropriate methods of calculating the pressure drop PD in tubes, internal fittings or packed beds, etc., may be found, for example, in the VDI-Wärmeatlas, 7th augmented edition, VDI-Verlag GmbH, Düsseldorf 1994, sections La1 to Lgb7, and also in the standard work by Heinz Brauer, Grundlagen der Einphasen- und Mehrphasenströmungen, Verlag Sauerländer, Aarau and Frankfurt am Main, 1971.

The pressure drop PD in the case of single-phase flow through an empty tube is given by $$PD=C_w \rho/2 w^2 D$$

where $\rho$ (kg/m$^3$): density of the flowing medium under operating conditions, w (m/s): flow velocity=volume of flow/cross-sectional area.

D (m): tube diameter $C_w$: resistance coefficient of the tube through which flow occurs In the case of flow through packing, beds or internal fittings, the velocity w is replaced by the effective velocity (w/$\psi$) and the tube diameter D is replaced by the hydraulic channel diameter $d_H$ of the packing or internal fittings, so that:

$$PD=C_w \rho/2(w/\psi)^2 1/d_H$$

where $d_H$ (m): hydraulic channel diameter $\psi$: empty tube fraction $C_w$: resistance coefficient of the apparatus with filling through which flow occurs.

The packing-related data $d_H$ and $\psi$ are frequently part of the delivery specifications for packing. For a series of packings, data are given in the above-mentioned VDI-Wärmeatlas.

The empty tube fraction $\psi$ can also be determined experimentally by, for example, measuring the capacity of the reactor before and after filling with the packing. The hydraulic channel diameter can in turn be calculated, if it is not known, from the specific surface area F (m$^2$/m$^3$) of the packing or internal fittings (generally known or able to be determined experimentally) using the simple relationship:

$$d_H=4\psi/F.$$

The resistance coefficient of tubes, internal fittings and packing is generally described as a function of the Reynolds number Re which gives information about the flow state under the chosen conditions. In the case of packing, internal fittings, etc., the following relationship can almost always be employed:

$$C_w=K_1/Re^n+K_2/Re^m$$

where frequently employed exponents are n=1, m=0 (method of S. Ergun, Chem. Engng. Progr. 48, (1948), 89) or n=1, m=0.1 (method of Brauer et al.). $K_1$, $K_2$ are packing-related constants which are known from supply data or from the literature (examples may be found in the VDI-W ärmeatlas and in Brauer et al.). However, they can also be determined experimentally by passing a liquid through the tube reactor containing packing at various velocities and determining $C_w$ as a function of Re from the known data and the measured pressure drop.

Finally the dimensionless Reynolds number Re is defined as Re=w($\rho/\eta$)D for empty tubes or Re=(w/$\psi$)($\rho/\eta$)$d_H$ for tubes containing internal fittings or packing. In each case, $\eta$ (Pa·s) is the viscosity and $\rho$ (kg/m$^3$) is the density of the flowing medium.

In the case of two-phase flows (here gas-liquid for synthesis gas/catalyst solution), the pressure drop increases overproportionally. Usually, using the Lockhart-Martinelli method (in Brauer et al.), the pressure drop of the two-phase flow $P_{lg}$ is expressed in relation to the pressure drop of one of the two phases, for example to the pressure drop of the pure flowing liquid phase $P_l$, and expressed in relation to the ratio of the pressure drop of the two phases $P_l$ and $P_g$ regarded as flowing alone.

To calculate pressure drops in two-phase flow, the dimensionless pressures $\phi^2=P_{lg}/P_l$ and $X^2=P_l/P_g$ are frequently used. The additional relationship $\phi^2$=function($X^2$) has also frequently been examined. Examples may be found in the following literature references:

Y. Sato, T. Hirose, F. Takahashi, M. Toda: "Pressure Loss and Liquid Hold Up in Packed Bed Reactor with Cocurrent Gas-Liquid Down Flow", J. Chem. Eng. Of Japan, Vol. 6 (No. 2), 1973, 147–152;

D. Sweeney: "A Correlation for Pressure Drop in Two-Phase Concurrent Flow in Packed Beds", AIChE Journal, Vol. 13, 7/1967, 663–669;

V. W. Weekman, J. E. Myers: "Fluid-Flow Characteristics of Cocurrent Gas-Liquid Flow in Packed Beds", AIChE Journal, Vol. 10 (No. 6), 11/1964, 951–957;

R. P. Larkins, R. P. White, D. W. Jeffrey: "Two-Phase Cocurrent Flow in Packed Beds", AIChE Journal, Vol. 7 (No. 2), 6/1961, 231–239 or N. Midoux, M. Favier, J. C. Charpentier: "Flow Pattern, Pressure Loss and Liquid Holdup Data in Gas-Liquid Downflow Packed Beds with Foaming and Nonfoaming Liquids"; J. Chem. Eng. Of Japan, Vol. 9 (No. 5), 1976, 350–356.

The relationship proposed by Midoux, which has been evaluated for many gas-liquid systems, is frequently utilized for the calculation. For example:

$$\phi^2=1+1/X+1.14X^{0.54}$$

This so-called Lockart-Martinelli relationship is depicted in graphical form in many works; detailed discussions of it may be found in many textbooks on process engineering and publications, for example in Brauer et al.

The pressure drop of the two-phase flow $P_{gl}$ is then derived from the experimentally determined pressure drop, or the pressure drop estimated as described above, of the pure flowing liquid phase $P_1$ using $$P_g/\phi^2 P_1.$$

In the present case of the preparation of aldehydes by hydroformylation of olefins, the calculation of the pressure drop is even more complex. Apart from the synthesis gas phase and a liquid catalyst phase, it is also necessary to take into account the presence of an organic liquid phase.

This problem can be solved by determining a further dimensionless pressure $\phi^2_{org} = P_{gll}/P_{lg}$, so that the pressure drop is determined as follows:

$$P_{gll} = \phi^2 \phi^2_{org} P_l$$

In general, expressed as a function of the reactor length L(m)

$$PD = P_g/L \text{ or } PD = P_{gll}/L.$$

The pressure drop of a multiphase flow can thus be calculated by customary methods of chemical engineering. The same applies to the previously defined dimensionless pressure drop B, i.e., the loading factor of the multiphase reactor.

The magnitude of the dimensionless loading factor B is a necessary fundamental condition in the process of the present invention; B should be greater than or equal to 0.8, preferably greater than or equal to 0.9 or particularly preferably greater than or equal to 1. In the region where B is greater than or equal to 0.8, a reactor operated from the top downwards begins to flood. When these conditions are used, the advantages of the process of the present invention are achieved even when the reactor is operated from the bottom upwards or in another direction.

Higher cross-sectional loadings of the reactor (B>>1), recognizable by the increasing differential pressure over the reactor, are possible at any time and even desirable as long as the increasing space-time yields justify the similarly increasing energy consumption. An upper limit is therefore imposed only by practical considerations such as energy consumption or difficulty of separating the phases after the reaction is complete.

It can thus be seen that, apart from the volume flow of the individual phases or the empty tube velocities $w = V(\pi D^2/4)$ derived therefrom, the physical dimensions of the reactor (length L, diameter D) and, in particular, the data for the packing used (hydraulic diameter $d_H$, empty tube fraction A) play an important role. With the aid of these parameters, the process can be adapted easily to a wide variety of requirements; it is only important to adhere to the condition $B \geq 0.8$, preferably $B \geq 0.9$ and particularly preferably $B \geq 1$.

When the rate of reaction is slow, the reactor may be packed with small hydraulic diameter packing materials or large specific surface area packing materials, so that the required conditions for B are achieved even at small flow velocities. In this way, one obtains sufficient residence times over the length of an industrial reactor of reasonable dimensions. When the rate of reaction is very fast, the reactor may be packed with relatively larger diameter packing materials, or relatively smaller specific surface area packing materials.

A further criterion for carrying out the process of the present invention is the ratio of the mass flow of the liquid, catalyst-containing phase $M_1$, to the mass flow of the disperse phase or phases $M_2$. For the present hydroformylation process, the mass flow of the catalyst phase $M_1$ is significantly greater than the mass flow of the dispersed phases, i.e. the organic olefin phase $M_{2a}$ and the synthesis gas phase $M_{2b}$. In the process of the present invention, the mass ratio $M_1/M_2$ of the continuous phase ($M_1$) to the dispersed phases ($M_2$) can be greater than 2; it is preferred that $M_1/M_2 > 10$. Flow ratios of $M_1/M_2 > 100$ are quite possible and frequently even advantageous. Under the condition $M_1/M_2 > 2$, the catalyst phase is the continuous phase, while the dispersed phases are divided into fine bubbles or fine droplets. In the process of the invention, it is possible for at least one starting material (olefin) to be dispersed by means of the energy introduced into the tube reactor by the continuous phase (catalyst). This leads to dispersion of at least one starting material as bubbles or droplets within the continuous catalyst phase.

This, too, can be estimated by means of customary engineering methods. Suitable methods employ relationships involving dimensionless parameters, for example $$d_S/d_H = k \text{Re}_{gl(gll)}{}^m \text{We}_{gl(gll)}{}^n$$

where $d_S$: diameter of the droplets or bubbles obtained by the Sauter method (described in Brauer et al.), $d_H$: hydraulic diameter of the packing, $\text{Re}_{gl(gll)}$: Reynolds number of the multiphase flow = $W_{gl(gll)}(\rho_1/\eta_1)(d_H/\Psi)$, $W_{gl(gll)}$: Weber number of the multiphase flow = $W_{gl(gll)}{}^2 (\rho_l/\sigma_{gl})(d_H/\Psi)^2$, k,m,n: empirical constants (known or determined by experiment), w: empty tube velocity (m/s) = $W(\pi D^2/4)$, V: volume flow under operating conditions (m$^3$/s), $\rho$: density under operating conditions (kg/m$^3$), $\eta$: viscosity under operating conditions (Pa·s) and $\gamma$: interfacial tension under operating conditions (N/m)

and the indices l (liquid phase), g (gas phase), gl (gas/liquid two-phase flow) and gll (gas/liquid/liquid three-phase flow).

In the case of structured packings such as Sulzer SMV or narrow tubes as internal fittings, it seems plausible that a calculated bubble or droplet diameter $d_S$ greater than the channel diameter is not reasonable. However, this does not apply to permeable packings and packing elements such as wire mesh rings or woven wire mesh (known as demister packings or droplet precipitators). In the process of the invention, it is possible to use calculated droplet diameters which are at least equal to or smaller than the hydraulic channel diameter:

$$d_S/d_H \leq 1, \text{ preferably} < 0.9.$$

The calculated droplet diameter finally allows a mass transfer area to be calculated in accordance with $$A_s = 6\phi_g d_s (m^2/m^3).$$

For the phase fraction $\phi_g$ of the dispersed phase (in the case of hydroformylation, the synthesis gas and/or organic phase are dispersed), the ratio of the empty tube velocities of the phases can be used:

$$\phi_g \sim w_g/w_{gl}.$$

The residence time $\tau$ of the phases flowing through the reactor can be calculated approximately as $\tau \sim L\psi/W_{lg}$. The residence time $\tau$ in the process of the present invention is generally much less than one hour and can be in the minute range or even lower. Nevertheless, this completely unusual method of operation (high catalyst throughput in the reactor, comparatively low proportion of starting material in the reaction composition, and as a result a very short residence time) achieves surprisingly high space-time yields. Alternatively, at the same space-time yields it is possible to work at significantly lower temperatures than is customary, because the increase in the reaction rate can, for example, result in minimization of secondary reactions and thus improve selectivity, thereby making this mode of operation economically feasible.

The process of the present invention can be adapted very flexibly to a wide variety of requirements. For example, if the application requires a very long mixing zone or calming zones are required, for example for decreasing mass flows, a cascaded arrangement of tube reactors having internal fittings or packing can be employed. A cascaded arrangement of tube reactors or the alternative arrangement of packed and empty tube sections may be used if a particularly low pressure drop is desired. Furthermore, a parallel arrangement of tube reactors or the use of a multitube reactor, in which the tubes can assume the function of internal fittings, can be used. In addition, reactors having multiple introduction of gas along the length of the reactor can be provided if the gas consumption is so high that unfavorable phase ratios of gas to liquid result from combining the two phases upstream of the reactor.

The particular conditions of the process of the present invention allow additional embodiments of the process. Thus, the necessity for high circulation rates of the catalyst phase or the continuous phase can be exploited to operate a jet nozzle which is located as a liquid jet gas compressor upstream of the actual tube reactor. This can be used for thorough premixing of the two phases and for compression of the gas phase, thereby making it possible to operate the reactor using higher addition pressures, particularly when gaseous olefins are employed as reactants. Finally, when suction is exploited rather than compressing the gas, circulation of gas with simultaneous premixing of the phases becomes possible. The energy introduced into the tube reactor by the catalyst-containing continuous phase can thus be used for dispersing the starting material phase or at least one starting material.

Heat removal is not a critical step in the process of the present invention. The high throughput of the catalyst phase acts as heat transfer medium so that, even in the case of adiabatic operation of the reactor, only small temperature differences are apparent in the reactor, and a homogeneous temperature distribution in the reactor results. The heat generated can then conveniently be removed or exploited for energy recovery by means of any conventional heat exchanger located externally in the catalyst circuit. To improve heat removal, it may be useful to run the catalyst circuit at a higher circulation rate (i.e., at a higher B value) than is technically necessary, thereby setting a smaller temperature gradient throughout the reactor.

The process of the present invention offers considerable advantages over those of the prior art. For example:

High space-time yields can be achieved at comparatively low temperatures;

The formation of by-products is extremely low—values of 1–2% by weight and below are possible;

The process conditions are very mild, and minimizes deactivation of the catalyst; continuous discharge is eliminated.

Additional advantages include:

The hydroformylation of higher olefins having more than 6 carbon atoms is economical because of the higher reaction rate;

When gaseous olefins are used as starting materials, the starting material remaining after partial conversion can be recycled by simple recirculation using a jet nozzle.

In the process of the present invention, the catalyst phase is the continuous phase. The mass ratio of catalyst phase to the dispersed phase or phases, i.e., the olefinic phase(s) at the reactor inlet, range from 5000/1 to 4/1, including 4000/1, 3000/1, 2000/1, 1000/1, 900/1, 800/1, 700/1, 600/1, 500/1, 400/1, 300/1, 200/1, and 100/1, inclusive of all values and subranges therebetween. Preferably, the mass ratio of the catalyst phase to the dispersed phase ranges from 2000/1 to 50/1. The mass ratio of catalyst phase to the hydroformylation agent (generally synthesis gas) is from 4/1 to 10,000/1, including 100/1, 200/1, 300/1, 400/1, 500/1, 600/1, 700/1, 800/1, 900/1, 1000/1, 2000/1, and 3000/1, inclusive of all values and subranges therebetween. Preferably, the mass ratio of the catalyst phase to the hydroformylation agent is from 200/1 to 4000/1.

The reactants can be preheated before being introduced into the reactor, i.e., in the region of the reaction temperature, or can be fed in cold. Owing to the high phase ratio of the catalyst phase to the reactants, preheating can also be carried out using process heat.

The process of the present invention is preferably carried out in a temperature range from 20° C. to 250° C., including 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., and 240° C., inclusive of all values and subranges therebetween. Temperatures of from 90° C. to 150° C. are particularly preferably. The total pressure is from 10 bar to 300 bar, including 20, 30, 40, 50, 60, 70, 80, 90, 100, 150, 200, and 250 bar, inclusive of all values and subranges therebetween. Preferably, the total pressure is from 20 bar to 150 bar.

The phases can flow through the tube reactor in a cocurrent mode from the top to the bottom or vice versa. For safety reasons, it is preferred to feed the phases into the reactor from the top.

The heat of reaction can be removed via various heat exchangers. The heat exchangers do not have to be in the vicinity of the reaction space, but can also, if desired, be located outside the reactor. The individual heat flows are dependent on the specific heat of reaction and on the desired temperatures in the reactor and in the work-up equipment.

The heat of reaction which has been removed can thus be utilized very simply, e.g., in the process itself, for heating a distillation apparatus, or for generating steam.

When gaseous olefins are used, or in the case of incomplete conversion, the mixture leaving the reactor can be degassed in a gas-liquid separation vessel. The gas-liquid separation can be carried out at the same pressure as at the reactor outlet. This is particularly advantageous when at least part of the gas removed is recirculated to the reactor. Otherwise, degassing can be carried out at lower pressures (e.g., down to 1 bar). The gas stream which has been separated off can be completely or partly recirculated to the reactor.

The recirculation of the gas stream can be achieved in a known manner, e.g., by means of a jet nozzle or mixing nozzle which is located in the catalyst circuit upstream of the reactor, or by means of a circulating gas compressor. Preferably, a jet nozzle or mixing nozzle which is located in the catalyst circuit upstream of the reactor is used to minimize energy consumption.

The remaining, or if desired, the total amount of gas can then be conveyed to a waste gas utilization system either after cooling or without any cooling. When the gas is cooled, the gas condensate obtained in the cooler can be conveyed via a line to the gas-liquid separation vessel.

The degassed liquid mixture is mechanically separated in a liquid—liquid separation vessel into catalyst phase and product phase. This can be carried out in settling vessels of various construction types, or in centrifuges. Settling vessels may be preferred to minimize cost.

Although the residence time of the liquid mixture in the separation apparatus is not critical, per se, it should preferably be kept short in order to minimize the size of the separation apparatus, and to reduce capital costs. In addition, when residence times are short, virtually no secondary reactions occur in the separation vessel. In order for the separation of the phases to occur quickly, the density difference between the two phases should be sufficiently large and their viscosities should be kept low. All three parameters are a function of the process temperature and can easily be optimized by carrying out initial experiments.

In addition, the density and viscosity of the catalyst solution can be varied by the choice of solvent and the catalyst concentration. In addition, the density and viscosity of the product phase may be adjusted by the addition of a solvent.

The phase separation step can be carried out over a wide temperature range. The separation temperature may be higher than the temperature of the reaction product at the outlet from the reactor, but, in order to conserve energy, it may be disadvantageous to employ a reaction temperature which is higher than the liquid temperature in the gas separator. The lowest possible separation temperature may be regarded as the pour point of one of the two liquid phases. However, in order to achieve short separation times, excessively low temperatures should not be selected.

The product stream can be fractionated by known methods, for example by distillation.

If desired, a small portion of the separated catalyst solution may be replaced by fresh catalyst solution, which is then typically recycled to the reactor.

Having generally described this invention, a further understanding can be obtained by reference to certain specific examples which are provided herein for purposes of illustration only, and are not intended to be limiting unless otherwise specified.

Hydroformylation of Propene:

EXAMPLE 1

(Comparative Example, Batch Reaction)

290.3 g of TPPTS ligand (triphenylphosphinetrisulphonate) in the form of its sodium salt, 31.8 g of propene and part of 291 g of a solvent consisting of 20% by weight of ethylene glycol and 80% by weight of water were placed at 120° C. in a stirred autoclave and 50 bar of synthesis gas were injected. The hydroformylation reaction was started by addition of 0.531 g of rhodium acetate dissolved in the remainder of the solvent. After complete conversion, which could be detected by means of the synthesis gas absorption curve, a liquid sample was taken from the reaction mixture. The composition of the mixture is shown below in Table 1.

TABLE 1

| Example 1 | |
| --- | --- |
| Example Substance | 1 Proportion in % by weight |
| Propene | 0.64 |
| i-Butyraldehyde | 5.90 |
| n-Butyraldehyde | 75.76 |
| n-Butanol | 1.69 |
| i-Propyl-1,3-dioxolane | 0.74 |
| n-Propyl-1,3-dioxolane | 7.33 |
| High boilers | 7.94 |

Figure 1:
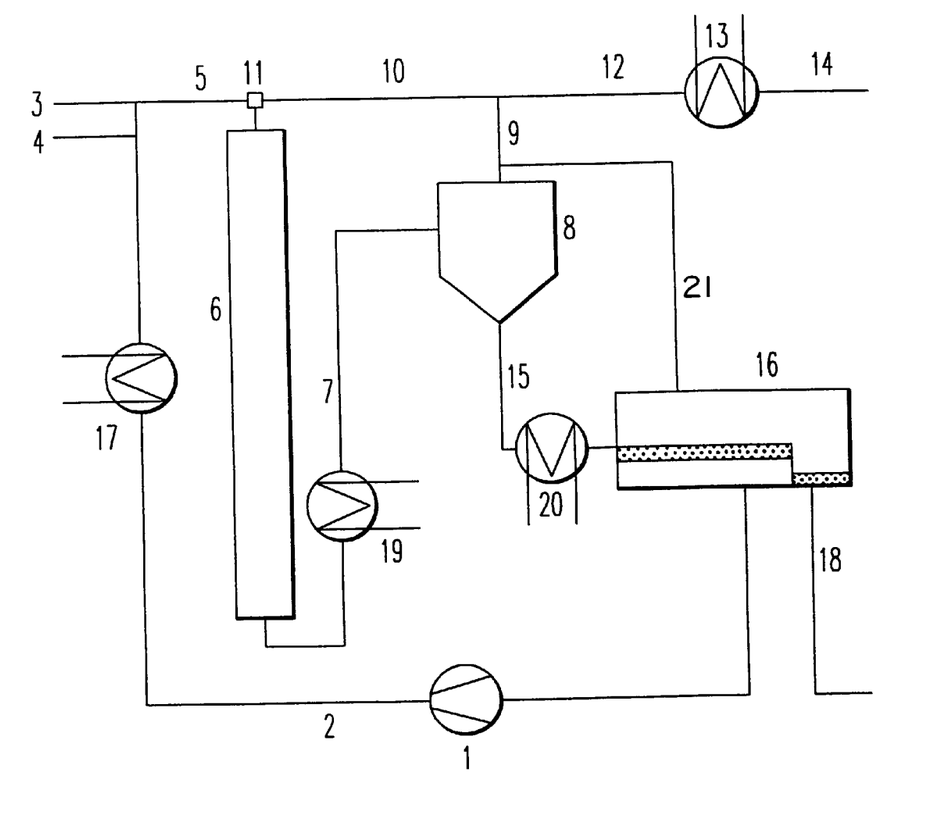
FIG. 1 is a schematic diagram of an apparatus for carrying out hydroformylation of an olefin according to the process of the present invention.

All continuous hydroformylation experiments (even those using a starting material other than propene) were carried out in an experimental apparatus as shown schematically in FIG. 1. Unless a different reactor is specified in the description of the example, a reactor having a length of 3 m and a diameter of 17.3 mm (volume: 705 ml) was used which contained static mixing elements from Sulzer having a hydraulic diameter of 2 mm. The aqueous catalyst was circulated by means of a pump 1. Olefin (e.g., propene) 3 and synthesis gas 4 were mixed into the catalyst solution. The multiphase mixture 5 obtained in this way was pumped via the mixing nozzle 11 through a tube reactor 6 which, as described above, was provided with static mixing elements. At this point, the intimate mixing of the phases, which is a function of the Reynolds number for given mixing elements, is particularly important. The resulting mixture 7, comprising product, unreacted starting material and the catalyst, was degassed in vessel 8. Most of the gas 9, comprising olefin (e.g., propene), synthesis gas and accumulated inert materials was then fed back to the reactor 6 via a gas return line 10 with the aid of a mixing nozzle 11. A small part of the gas stream 9 was bled off via a line 12. By means of appropriate coolant 13 and recirculation of the supercritical propane, the bleed stream 14 was reduced to contain mainly accumulated inert materials and small amounts of unreacted synthesis gas. As a result of this arrangement, the conversion of olefin (e.g., propene) was virtually unaffected by the discharge of inert materials.

The liquid stream 15 obtained after degassing in the vessel 8 was then conveyed to a phase separation vessel 16, where the aqueous catalyst phase 2 was separated off and returned to the circuit. The heat of reaction may be removed by means of an external heat exchanger 17.

The product is taken off via line 18. Line 21 feeds the off gas for recycling by way of lines 9 and 10.

EXAMPLES 2 TO 5

(Comparative Examples, Continuous Process Without Solvent Mixture)

These examples represent comparative experiments in the continuous apparatus described above in which a purely aqueous solvent system was used. These comparative examples demonstrate the improved space-time yield of the process of the present invention.

For these examples, line 10 for recirculating the gas was closed, and water was used as solvent for the catalyst. 400 kg/h of catalyst flowed through the 705 ml reactor at a temperature of 120° C. The reaction pressure was 50 bar. The concentration of rhodium was 800 ppm based on the solvent phase. TSTPP was used as the ligand for the rhodium catalyst, in the form of its sodium salt (NaTSTPP); the P/Rh ratio was 60.

Example 3 was carried out under the reaction conditions of Example 2, except that the reaction temperature was 130° C.

Example 4 was carried out under the reaction conditions of Example 2, except that the reaction pressure was 70 bar.

Example 5 was carried out under the reaction conditions of Example 2, except that 300 kg/h of catalyst were passed through the reactor. The molar flows of starting materials fed in and of the products are shown in the Table 2, below, in units of mol/h.

TABLE 2

Comparative Examples 2–5

| | Example | | | |
|---|---|---|---|---|
| | 2 | 3 | 4 | 5 |
| STY (te/(m³h)) | 0.98 | 1.39 | 1.23 | 0.71 |
| Starting material | | | | |
| CO | 22.79 | 16.99 | 28.24 | 12.73 |
| $H_2$ | 21.28 | 15.87 | 26.38 | 11.89 |
| $N_2$ | 0.12 | 0.09 | 0.15 | 0.07 |
| Propene | 51.49 | 35.57 | 31.13 | 33.45 |
| Propane | 0.17 | 0.12 | 0.10 | 0.11 |
| Product | | | | |
| CO | 2.15 | 2.09 | 2.08 | 2.11 |
| $H_2$ | 0.89 | 0.93 | 0.98 | 0.97 |
| Propene | 3.35 | 6.73 | 3.04 | 4.00 |
| i-Butanal | 0.24 | 0.51 | 0.53 | 0.20 |
| n-Butanal | 5.46 | 11.03 | 9.82 | 4.66 |
| i-Butanol | <0.01 | <0.01 | <0.01 | <0.01 |
| n-Butanol | 0.07 | 0.07 | 0.07 | 0.07 |
| 2-Ethylhexanal | 0.09 | 0.03 | 0.08 | 0.02 |
| 2-Ethylhexenal | 0.26 | 0.19 | 0.18 | 0.09 |
| Off-gas | | | | |
| CO | 9.50 | 3.06 | 13.23 | 6.81 |
| $H_2$ | 8.45 | 1.46 | 9.97 | 3.59 |
| $N_2$ | 0.29 | 0.10 | 0.09 | 0.16 |
| Propene | 37.37 | 13.56 | 17.72 | 36.93 |
| Propane | 0.17 | 0.10 | 0.17 | 0.09 |
| i-Butanal | 0.08 | 0.08 | 0.03 | 0.01 |
| n-Butanal | 4.59 | 3.13 | 2.72 | 2.56 |

EXAMPLES 6 TO 11

(According to the Present Invention)

These examples describe the process of the present invention, in which a solvent mixture of water/ethylene glycol is used in the continuous apparatus described above. The measured data shows that increased space-time yields are obtained compared to the Comparative Examples, above. In addition, and in contrast to stirred systems, there was no appreciable formation of dioxolanes.

Example 6 was carried out under the reaction conditions of Example 5, except that a mixture of water and ethylene glycol (20% by weight) was used as solvent.

In Example 7, the concentration of ethylene glycol was increased to 40% by weight.

Example 8 was carried out under the reaction conditions of Example 7, except that 400 kg/in of catalyst were passed through the reactor and the reaction temperature was 130° C.

Example 9 was carried out under the reaction conditions of Example 8, except that the reaction temperature was 120° C. and the reaction pressure was 70 bar.

Example 10 was carried out under the reaction conditions of Example 9, except that the reaction temperature was 90° C. This experiment demonstrates that it is possible to carry out the hydroformylation of propene in a multiphase system at high space-time yields even at low temperatures.

Example 11 was carried out under the reaction conditions of Experiment 10, except that the reaction pressure was 50 bar and the rhodium concentration was 200 ppm, based on the solvent. This experiment demonstrates that it is possible to carry out the hydroformylation of propene in a multiphase system at high space-time yields even when using low rhodium concentrations. The molar flows of starting materials fed in and of the products are shown in Table 3 in units of mol/h.

TABLE 3

Examples 6–11

| | Example | | | | | |
|---|---|---|---|---|---|---|
| | 6 | 7 | 8 | 9 | 10 | 11 |
| STY (te/(m³h)) | 1.3 | 1.7 | 3.8 | 2.3 | 0.3 | 0.5 |
| Starting material | | | | | | |
| CO | 23.31 | 23.28 | 53.28 | 45.72 | 22.96 | 23.23 |
| $H_2$ | 21.40 | 21.57 | 49.16 | 42.38 | 21.70 | 21.33 |
| $N_2$ | 0.12 | 0.11 | 0.25 | 0.20 | 0.12 | 0.09 |
| Propene | 49.88 | 35.20 | 59.35 | 42.89 | 38.04 | 35.59 |
| Propane | 0.12 | 0.08 | 0.12 | 0.09 | 0.08 | 0.07 |
| Product | | | | | | |
| CO | 2.25 | 8.55 | 2.05 | 2.50 | 0.61 | 0.29 |
| $H_2$ | 0.83 | 1.51 | 0.41 | 1.02 | 0.16 | 0.10 |
| Propene | 4.37 | 5.38 | 6.33 | 4.14 | 0.51 | 0.18 |
| i-Butanal | 0.55 | 1.20 | 3.47 | 2.13 | 0.06 | 0.03 |
| n-Butanal | 9.34 | 17.25 | 36.99 | 21.60 | 0.96 | 0.52 |
| i-Butanol | 0.00 | 0.00 | 0.03 | 0.02 | 0.00 | 0.00 |
| n-Butanol | 0.06 | 0.15 | 0.48 | 0.23 | 0.01 | 0.00 |
| i-Propyldioxolane | <0.01 | 0.02 | 0.04 | 0.03 | <0.01 | <0.01 |
| n-Propyldioxolane | 0.05 | 0.21 | 0.46 | 0.37 | 0.13 | 0.12 |
| 2-Ethylhexanal | 0.20 | 0.21 | 0.46 | 0.39 | 0.08 | 0.05 |
| 2-Ethylhexenal | 0.41 | 0.50 | 0.60 | 0.58 | 0.10 | 0.17 |
| Off-gas | | | | | | |
| CO | 9.09 | 3.15 | 5.79 | 16.42 | 18.42 | 18.37 |
| $H_2$ | 5.05 | 1.20 | 1.85 | 11.61 | 14.90 | 14.29 |
| $N_2$ | 0.22 | 0.09 | 0.33 | 0.25 | 0.13 | 0.12 |
| Propene | 30.09 | 6.31 | 9.21 | 13.04 | 35.28 | 34.04 |
| Propane | 0.18 | 0.06 | 0.17 | 0.20 | 0.10 | 0.10 |
| i-Butanal | 0.09 | 0.04 | 0.01 | 0.26 | 0.13 | 0.20 |
| n-Butanal | 3.43 | 0.36 | 1.35 | 1.87 | 1.61 | 2.95 |

Selective Hydroformylation of 1-Butene

A further application of the process of the invention is the selective hydroformylation of 1-butene from a raffinate I mixture. This mixture comprises $C_4$-olefins and $C_4$-paraffins and contains 26–29% by weight of 1-butene. The catalyst solvent selected was a mixture of water and ethylene glycol (50/50% by weight).

EXAMPLE 12

(Comparative Example, Batch Process)

This experiment is a comparative example carried out in a stirred autoclave in order to demonstrate that processes employing conventional stirred reactors provide poorer product quality than the process of the present invention. 29.81 g of NaTSTPP, 86.2 g of 1-butene, 13.5 g of isobutane and 67.7 g of a solvent consisting of 30% by weight of ethylene glycol and 70% by weight of water were placed at 105° C. in a stirred autoclave and 30 bar of synthesis gas was injected. The hydroformylation reaction was started by addition of 2.09 g of a rhodium acetate solution containing 3.7% of Rh (in 30% by weight of ethylene glycol and 70% by weight of water). After complete conversion, which could be detected by means of the synthesis gas absorption curve, a liquid sample was taken from the reaction mixture. In Table 4, below, isobutane served as internal standard, and was disregarded in the calculation.

Table 4

| Example 12 | |
| --- | --- |
| Example | 12 |
| Substance | Proportion in % by weight |
| 1-Butene | 6.1 |
| 2-Methylbutanal | 1.19 |
| Pentanal | 77.4 |
| i-Propyl-1,3-dioxolane | 0.13 |
| n-Propyl-1,3-dioxolane | 11.9 |
| Remainder | 3.28 |

The continuous hydroformylation of 1-butene in Examples 13 to 26 was carried out in the same way as the hydroformylation of propene except that the gas return line 10 was closed.

EXAMPLE 13

This example describes the use of a solvent mixture of 50% by weight of water and 50% by weight of ethylene glycol in the continuous apparatus described above, according to the present invention. The data obtained shows that the amount of dioxolanes formed in the process is greatly reduced compared with stirred systems. 400 kg/h of catalyst were passed through the 3 m long reactor at a temperature of 115° C. In addition, 600 standard l/h of synthesis gas and 3 kg/h of raffinate I were fed in. The reaction pressure was 50 bar. The data obtained are shown in Table 5, below.

TABLE 5

| Example 13 | |
| --- | --- |
| Example | 13 |
| 1-Butene, % by weight in feed | 27.00 |
| C (1-butene) | 64.68% |
| STY (te/m$^3$/h) | 0.74 |
| Product: | |
| i-Butane | 1.39 |
| n-Butane | 5.77 |
| Cyclobutane | 0.04 |
| trans-Butene | 5.93 |
| 1-Butene | 5.07 |
| Isobutene | 21.77 |
| cis-Butene | 4.14 |
| Neopentane | 0.04 |
| 1,3-Butadiene | 0.00 |
| 2-Methylbutanal | 1.88 |
| 3-Methylbutanal | 5.28 |
| n-Pentanal | 42.58 |
| 2-Methylbutanol | 0.12 |
| Methylpropyldioxolane | 0.09 |
| 1-Pentanol | 0.41 |
| 2-n-Butyl-1,3-dioxolane | 0.25 |
| Ethylene glycol | 0.03 |

EXAMPLE 14

This example was carried out under the conditions of Example 13, except that 200 kg/h of catalyst was passed through the reactor. The results obtained are shown in Table 6, below.

Table 6

| Example 14 | |
| --- | --- |
| Example | 14 |
| 1-Butene, % by weight in feed | 27.30 |

Table 6-continued

| Example 14 | |
| --- | --- |
| C (1-butene) | 59.46% |
| STY (te/m$^3$/h) | 0.69 |
| Product: | |
| i-Butane | 3.10 |
| n-Butane | 9.71 |
| Cyclobutane | 0.06 |
| trans-Butene | 8.55 |
| 1-Butene | 9.50 |
| Isobutene | 35.98 |
| cis-Butene | 5.60 |
| Neopentane | 0.06 |
| 1,3-Butadiene | 0.00 |
| 2-Methylbutanal | 1.03 |
| 3-Methylbutanal | 2.25 |
| n-Pentanal | 22.07 |
| 2-Methylbutanol | <0.01 |
| Methylpropyldioxolane | <0.01 |
| 1-Pentanol | 0.22 |
| 2-n-Butyl-1,3-dioxolane | 0.23 |
| Ethylene glycol | <0.01 |

EXAMPLE 15

This example was carried out under the reaction conditions of Example 13, except that 100 kg/h of catalyst were passed through the reactor and the reaction temperature was 85° C. The results are shown in Table 7, below.

TABLE 7

| Example 15 | |
| --- | --- |
| Example | 15 |
| 1-Butene, % by weight in feed | 28.90 |
| C (1-butane) | 17.09% |
| STY (te/m$^3$/h) | 0.21 |
| Product: | |
| i-Butane | 1.98 |
| n-Butane | 10.50 |
| Cyclobutane | 0.07 |
| trans-Butene | 9.89 |
| 1-Butene | 22.17 |
| Isobutene | 37.42 |
| cis-Butene | 6.19 |
| Neopentane | 0.09 |
| 1,3-Butadiene | 0.11 |
| 2-Methylbutanal | 0.29 |
| 3-Methylbutanal | 0.48 |
| n-Pentanal | 9.61 |
| 2-Methylbutanol | 0.03 |
| Methylpropyldioxolane | 0.03 |
| 1-Pentanol | 0.23 |
| 2-n-Butyl-1,3-dioxolane | 0.19 |
| Ethylene glycol | <0.01 |

EXAMPLE 16

This example was carried out under the reaction conditions of Example 13, except that 250 kg/h of catalyst were passed through the reactor and the reaction temperature was 85° C. The results are shown in Table 8, below.

TABLE 8

| Example 16 | |
| --- | --- |
| Example | 16 |
| 1-Butene, % by weight in feed | 28.90 |

TABLE 8-continued

| Example 16 | |
|---|---|
| C (1-butane) | 20.98% |
| STY (te/m³/h) | 0.26 |
| Product: | |
| i-Butane | 1.88 |
| n-Butane | 8.53 |
| Cyclobutane | 0.06 |
| trans-Butene | 8.88 |
| 1-Butene | 17.07 |
| Isobutene | 28.61 |
| cis-Butene | 5.48 |
| Neopentane | 0.09 |
| 1,3-Butadiene | 0.00 |
| 2-Methylbutanal | 0.77 |
| 3-Methylbutanal | 0.68 |
| n-Pentanal | 27.55 |
| 2-Methylbutanol | 0.05 |
| Methylpropyldioxolane | 0.01 |
| 1-Pentanol | 0.11 |
| 2-n-Butyl-1,3-dioxolane | 0.04 |
| Ethylene glycol | <0.01 |

EXAMPLE 17

This example was carried out under the reaction conditions of Example 13. except that the reaction temperature was 90° C. The results are shown in Table 9, below.

TABLE 9

| Example 17 | |
|---|---|
| Example | 17 |
| 1-Butene, % by weight in feed | 28.90 |
| C (1-butene) | 27.11% |
| STY (te/m³/h) | 0.33 |
| Product: | |
| i-Butane | 2.19 |
| n-Butane | 8.97 |
| Cyclobutane | 0.06 |
| trans-Butene | 8.94 |
| 1-Butene | 17.11 |
| Isobutene | 32.67 |
| cis-Butene | 5.53 |
| Neopentane | 0.07 |
| 1,3-Butadiene | 0.00 |
| 2-Methylbutanal | 0.76 |
| 3-Methylbutanal | 0.57 |
| n-Pentanal | 22.99 |
| 2-Methylbutanol | 0.05 |
| Methylpropyldioxolane | 0.00 |
| 1-Pentanol | 0.07 |
| 2-n-Butyl-1,3-dioxolane | 0.03 |
| Ethylene glycol | <0.01 |

EXAMPLE 18

This example was carried out under the reaction conditions of Example 13, except that the reaction temperature was 70° C. The results are shown in Table 10, below.

TABLE 10

| Example 18 | |
|---|---|
| Example | 18 |
| 1-Butene, % by weight in feed | 27.00 |
| C(1-butene) | 9.39% |
| STY (te/m³h)) | 0.11 |

TABLE 10-continued

| Example 18 | |
|---|---|
| Product: | |
| i-Butane | 2.51 |
| n-Butane | 10.96 |
| Cyclobutane | 0.06 |
| trans-Butene | 9.80 |
| 1-Butene | 23.13 |
| Isobutene | 39.01 |
| cis-Butene | 6.38 |
| Neopentane | 0.06 |
| 1,3-Butadiene | 0.17 |
| 2-Methylbutanal | 0.24 |
| 3-Methylbutanal | 0.63 |
| n-Pentanal | 4.79 |
| 2-Methylbutanol | 0.02 |
| Methylpropyldioxolane | 0.08 |
| 1-Pentanol | 0.3 |
| 2-n-Butyl-1,3-dioxolane | 0.31 |
| Ethylene glycol | <0.01 |

EXAMPLE 19

This example was carried out under the reaction conditions of Example 13, except that the reaction temperature was 80° C. The results are shown in Table 11, below.

TABLE 11

| Example 19 | |
|---|---|
| Example | 19 |
| 1-Butene, % by weight in feed | 27.00 |
| C(1-butane) | 19.71% |
| STY (te/(m³h)) | 0.23 |
| Product: | |
| i-Butane | 2.01 |
| n-Butane | 10.91 |
| Cyclobutane | 0.08 |
| trans-Butene | 11.71 |
| 1-Butene | 18.23 |
| Isobutene | 28.57 |
| cis-Butene | 8.01 |
| Neopentane | 0.12 |
| 1,3-Butadiene | 0.15 |
| 2-Methylbutanal | 0.67 |
| 3-Methylbutanal | 0.41 |
| n-Pentanal | 17.79 |
| 2-Methylbutanol | 0.04 |
| Methylpropyldioxolane | 0.04 |
| 1-Pentanol | 0.25 |
| 2-n-Butyl-1,3-dioxolane | 0.02 |
| Ethylene glycol | <0.01 |

EXAMPLE 20

This example was carried out under the reaction conditions of Example 13, except that the reaction temperature was 85° C. The results are shown in Table 12, below.

TABLE 12

| Example 20 | |
|---|---|
| Example | 20 |
| 1-Butene, % by weight in feed | 27.00 |
| C (1-butene) | 24.23% |
| STY (te/(m³h)) | 0.28 |

TABLE 12-continued

Example 20

Product:

| | |
|---|---|
| i-Butane | 1.68 |
| n-Butane | 9.18 |
| Cyclobutane | 0.06 |
| trans-Butene | 9.01 |
| 1-Butene | 16.27 |
| Isobutene | 31.89 |
| cis-Butene | 6.34 |
| Neopentane | 0.07 |
| 1,3-Butadiene | 0.09 |
| 2-Methylbutanal | 0.78 |
| 3-Methylbutanal | 0.47 |
| n-Pentanal | 19.07 |
| 2-Methylbutanol | 0.06 |
| Methylpropyldioxolane | 0 |
| 1-Pentanol | 0.15 |
| 2-n-Butyl-1,3-dioxolane | 0.03 |
| Ethylene glycol | <0.01 |

EXAMPLE 21

This example was carried out under the reaction conditions of Example 13, except that the reaction temperature was 95° C. The results are shown in Table 13, below.

TABLE 13

Example 21

| | |
|---|---|
| Example | 21 |
| 1-Butene, % by weight in feed | 27.00 |
| C (1-butene) | 32.66% |
| STY (te/(m$^3$h)) | 0.38 |

Product:

| | |
|---|---|
| i-Butane | 1.90 |
| n-Butane | 9.81 |
| Cyclobutane | 0.07 |
| trans-Butene | 10.01 |
| 1-Butene | 14.99 |
| Isobutene | 31.62 |
| cis-Butene | 7.04 |
| Neopentane | 0.08 |
| 1,3-Butadiene | 0.07 |
| 2-Methylbutanal | 0.82 |
| 3-Methylbutanal | 0.75 |
| n-Pentanal | 22.39 |
| 2-Methylbutanol | 0.05 |
| Methylpropyldioxolane | 0.01 |
| 1-Pentanol | 0.09 |
| 2-n-Butyl-1,3-dioxolane | 0.02 |
| Ethylene glycol | <0.01 |

EXAMPLE 22

This example was carried out under the reaction conditions of Example 13, except that the reaction temperature was 105° C. The results are shown in Table 14, below.

TABLE 14

Example 22

| | |
|---|---|
| Example | 22 |
| 1-Butene, % by weight in feed | 27.00 |
| C (1-butene) | 44.34% |
| STY (te/(m$^3$h)) | 0.51 |

TABLE 14-continued

Example 22

Product:

| | |
|---|---|
| i-Butane | 2.09 |
| n-Butane | 9.47 |
| Cyclobutane | 0.06 |
| trans-Butene | 8.97 |
| 1-Butene | 12.56 |
| Isobutene | 34.63 |
| cis-Butene | 6.24 |
| Neopentane | 0.06 |
| 1,3-Butadiene | 0.05 |
| 2-Methylbutanal | 0.85 |
| 3-Methylbutanal | 1.08 |
| n-Pentanal | 21.35 |
| 2-Methylbutanol | 0.05 |
| Methyipropyldioxolane | 0.00 |
| 1-Pentanol | 0.12 |
| 2-n-Butyl-1,3-dioxolane | 0.04 |
| Ethylene glycol | <0.01 |

EXAMPLE 23

This example was carried out under the reaction conditions of Example 13, except that the reaction temperature was 115° C. The results are shown in Table 15, below.

TABLE 15

Example 23

| | |
|---|---|
| Example | 23 |
| 1-Butene, % by weight in feed | 28.10 |
| C (1-butene) | 66.66% |
| STY (te/(m$^3$h)) | 0.80 |

Product:

| | |
|---|---|
| i-Butane | 1.71 |
| n-Butane | 7.77 |
| Cyclobutane | 0.05 |
| trans-Butene | 7.37 |
| 1-Butene | 6.19 |
| Isobutene | 26.46 |
| cis-Butene | 4.87 |
| Neopentane | 0.03 |
| 1,3-Butadiene | 0.00 |
| 2-Methylbutanal | 1.8 |
| 3-Methylbutanal | 4.65 |
| n-Pentanal | 36.17 |
| 2-Methylbutanol | 0.09 |
| Methylpropyldioxolane | 0.1 |
| 1-Pentanol | 0.41 |
| 2-n-Butyl-1,3-dioxolane | 0.47 |
| Ethylene glycol | <0.01 |

EXAMPLE 24

This example was carried out under the reaction conditions of Example 13, except that the reaction pressure was 33 bar. The results are shown in Table 16, below.

TABLE 16

Example 24

| | |
|---|---|
| Example | 24 |
| 1-Butene, % by weight in feed | 28.30 |
| C (1-butene) | 52.86% |
| STY (te/(m$^3$h)) | 0.64 |

TABLE 16-continued

Example 24

| Product: | |
|---|---|
| i-Butane | 2.63 |
| n-Butane | 10.63 |
| Cyclobutane | 0.06 |
| trans-Butene | 10.22 |
| 1-Butene | 12.20 |
| Isobutene | 35.78 |
| cis-Butene | 7.45 |
| Neopentane | 0.03 |
| 1,3-Butadiene | 0.01 |
| 2-Methylbutanal | 0.48 |
| 3-Methylbutanal | 1.3 |
| n-Pentanal | 17.64 |
| 2-Methylbutanol | 0.04 |
| Methylpropyldioxolane | <0.01 |
| 1-Pentanol | 0.14 |
| 2-n-Butyl-1,3-dioxolane | 0.15 |
| Ethylene glycol | <0.01 |

EXAMPLE 25

This example was carried out under the reaction conditions of Example 13. except that the reaction pressure was 43 bar. The results are shown in Table 17, below.

TABLE 17

Example 25

| Example | 25 |
|---|---|
| 1-Butene, % by weight in feed | 28.30 |
| C(1-butene) | 58.59% |
| STY (te/(m³h)) | 0.71 |
| Product: | |
| i-Butane | 1.67 |
| n-Butane | 8.02 |
| Cyclobutane | 0.05 |
| trans-Butene | 8.37 |
| 1-Butene | 7.90 |
| Isobutene | 24.87 |
| cis-Butene | 6.20 |
| Neopentane | 0.04 |
| 1,3-Butadiene | 0.01 |
| 2-Methylbutanol | 1.29 |
| 3-Methylbutanal | 5.18 |
| n-Pentanal | 30.29 |
| 2-Methylbutanol | 0.04 |
| Methylpropyldioxolane | 0.47 |
| 1-Pentanol | 0.79 |
| 2-n-Butyl-1,3-dioxolane | 1.48 |
| Ethylene glycol | <0.01 |

EXAMPLE 26

This example was carried out under the reaction conditions of Example 13, except that the reactor length was 1 m. The results are shown in Table 18, below.

TABLE 18

Example 26

| Example | 26 |
|---|---|
| 1-Butene, % by weight in feed | 27.60 |
| C (1-butane) | 62.22% |
| STY (te/m³/h) | 0.73 |

TABLE 18-continued

Example 26

| Product: | |
|---|---|
| i-Butane | 2.11 |
| n-Butane | 8.16 |
| Cyclobutane | 0.06 |
| trans-Butene | 8.50 |
| 1-Butene | 7.14 |
| Isobutene | 25.78 |
| cis-Butene | 5.50 |
| Neopentane | 0.05 |
| 1,3-Butadiene | 0.01 |
| 2-Methylbutanal | 1.64 |
| 3-Methylbutanal | 4.57 |
| n-Pentanal | 33.65 |
| 2-Methylbutanol | 0.07 |
| Methylpropyldioxolane | 0.09 |
| 1-Pentanol | 0.41 |
| 2-n-Butyl-1,3-dioxolane | 0.34 |
| Ethylene glycol | <0.01 |

EXAMPLE 27

This example was carried out under the reaction conductions of Example 13, except that the reactor length was 2 m (with the same internal fittings and diameter). The results are shown in Table 19, below.

TABLE 19

Example 27

| Example | 27 |
|---|---|
| 1-Butene, % by weight in feed | 27.60 |
| C (1-butene) | 62.53% |
| STY (te/m³/h) | 0.73 |
| Product: | |
| i-Butane | 1.38 |
| n-Butane | 6.41 |
| Cyclobutane | 0.04 |
| trans-Butene | 7.16 |
| 1-Butene | 6.02 |
| Isobutene | 22.28 |
| cis-Butene | 5.35 |
| Neopentane | 0.05 |
| 1,3-Butadiene | 0.01 |
| 2-Methylbutanal | 1.34 |
| 3-Methylbutanal | 3.36 |
| n-Pentanal | 36.93 |
| 2-Methylbutanol | 0.04 |
| Methylpropyldioxolane | <0.03 |
| 1-Pentanol | 0.61 |
| 2-n-Butyl-1,3-dioxolane | 0.43 |
| Ethylene glycol | <0.01 |

Hydroformylation of 1-Decene

In Examples 28 and 29, 400 kg/h of catalyst solution were passed through the reactor of the experimental apparatus. The reaction temperature was 125° C. and the reaction pressure was 70 bar. The concentration of the rhodium was 800 ppm, based on the catalyst phase. TSTPP, in the form of its sodium salt, was used as the ligand.

EXAMPLE 28

(Comparative Example, Continuous Process Without Solvent Mixture)

Water was used as solvent for the catalyst, at a pH of 4.5. The P/Rh ratio in the catalyst was 5. The molar flow rates of starting materials and of the products, in units of mol/h, are shown in Table 20.

TABLE 20

Example 28

| | |
|---|---|
| Example | 28 |
| STY (te/m$^3$h)) | 0.05 |
| B | 13.96 |
| Starting material | |
| CO | 11.38 |
| H$_2$ | 10.52 |
| N$_2$ | 0.05 |
| 1-Decene | 7.12 |
| Product | |
| 1-Decene | 6.67 |
| Undecanal | 0.34 |
| 2-Methyldecanal | 0.11 |
| Off-gas | |
| CO | 10.36 |
| N$_2$ | 9.89 |
| N$_2$ | 0.05 |

EXAMPLE 29

Example 29 describes the use, according to the invention, of a solvent mixture of 50% by weight of water and 50% by weight of ethylene glycol for the hydroformylation of 1-decene in order to demonstrate that the process of the present invention provides superior space-time yields relative to processes employing only water as the solvent.

The solvent used for the catalyst was a mixture of water and ethylene glycol (1:1) at a pH of 7.3. The P/Rh ratio in the catalyst was 60. The molar flow rates of starting materials and of the products, in units if mol/h, are shown in Table 21.

TABLE 21

Example 29

| | |
|---|---|
| Example | 29 |
| STY (te/m$^3$h)) | 0.08 |
| B | 12.94 |
| Starting material | |
| CO | 13.86 |
| H$_2$ | 12.86 |
| N$_2$ | 0.06 |
| 1-Decene | 7.33 |
| Product | |
| 1-Decene | 6.65 |
| Undecanal | 0.61 |
| 2-Methyldecanal | 0.04 |
| Off-gas | |
| CO | 12.92 |
| N$_2$ | 12.27 |
| N$_2$ | 0.07 |

The priority document of the present application, German patent application 19957528.2 filed Nov. 30, 1999, is incorporated herein by reference.

What is claimed as new and intended to be secured by Letters Patent is:

1. A hydroformylation process comprising:

reacting, in a tube reactor, a multiphase mixture of starting materials comprising one or more olefins having from 2 to 25 carbon atoms, hydrogen, and carbon monoxide, in the presence of a hydroformylation catalyst, wherein said multiphase mixture further comprises a continuous liquid phase and at least one dispersed phase, said catalyst is present in said continuous phase, said continuous phase comprises a solvent mixture, at least one olefin is present in said dispersed phase, said tube reactor has a loading factor which is equal to or greater than 0.8, and wherein at least one component of the solvent mixture comprises a polar organic compound having at least two oxygen atoms.

2. The process of claim 1, wherein said solvent mixture has a dielectric constant of from 50 to 78.

3. The process of claim 1, wherein said solvent mixture comprises water and a water-miscible organic solvent containing at least two oxygen atoms.

4. The process of claim 1, wherein said catalyst comprises a transition metal of Group VIII of the Periodic Table of the Elements.

5. The process of claim 1, wherein said catalyst comprises rhodium.

6. The process of claim 5, wherein said catalyst comprises a water-soluble rhodium compound.

7. The process of claim 1, wherein said loading factor is greater than or equal to 0.9.

8. The process of claim 1, wherein said loading factor is greater than or equal to 1.0.

9. The process of claim 1, wherein the ratio of the mass of said continuous phase to the sum of the masses of said at least one dispersed phase is greater than 2.

10. The process of claim 1, wherein said continuous phase flows through a jet nozzle located upstream of said tube reactor.

11. The process of claim 1, wherein at least one of said starting materials is dispersed by said continuous phase.

12. A process for preparing a carboxylic acid comprising:

preparing an aldehyde according to the process of claim 1, and oxidizing said aldehyde, thereby forming a carboxylic acid.

13. A process for preparing an alcohol comprising:

preparing an aldehyde according to the process of claim 1, and reducing said aldehyde, thereby forming an alcohol.

14. A process for preparing an aldol condensation product comprising:

preparing an aldehyde according to the process of claim 1, and condensing said aldehyde with a base catalyst, thereby forming an aldol condensation product.

15. The process of claim 1, wherein the product of the hydroformylation process is present in a phase other than the phase containing the catalyst.

* * * * *